US012758283B2

(12) United States Patent
Reinauer et al.

(10) Patent No.: US 12,758,283 B2
(45) Date of Patent: Oct. 13, 2026

(54) RHOMBUS-FORMING MAXILLA REPOSITIONING IMPLANT

(71) Applicant: Karl Leibinger Asset Management GMBH & CO. KG, Mühlheim (DE)

(72) Inventors: Frank Reinauer, Emmingen-Liptingen (DE); Lorenz Gabele, Sauldorf (DE)

(73) Assignee: Karl Leibinger Asset Management GMBH & CO. KG, Mühlheim (DE)

( * ) Notice: Subject to any disclaimer, the term of this patent is extended or adjusted under 35 U.S.C. 154(b) by 390 days.

(21) Appl. No.: 18/246,965

(22) PCT Filed: Dec. 13, 2021

(86) PCT No.: PCT/EP2021/085559
§ 371 (c)(1),
(2) Date: Mar. 28, 2023

(87) PCT Pub. No.: WO2022/128961
PCT Pub. Date: Jun. 23, 2022

(65) Prior Publication Data
US 2023/0363806 A1 Nov. 16, 2023

(30) Foreign Application Priority Data
Dec. 18, 2020 (DE) ..................... 10 2020 134 240.3

(51) Int. Cl.
*A61B 17/80* (2006.01)
*A61B 17/68* (2006.01)

(52) U.S. Cl.
CPC .......... *A61B 17/8071* (2013.01); *A61B 17/68* (2013.01); *A61B 2017/681* (2013.01)

(58) Field of Classification Search
CPC ............................................ A61B 17/80–809
See application file for complete search history.

(56) References Cited

U.S. PATENT DOCUMENTS 4,429,690 A * 2/1984 Angelino-Pievani ........................ A61B 17/80 606/280
6,093,188 A * 7/2000 Murray ............. A61B 17/8085 606/285

(Continued)

FOREIGN PATENT DOCUMENTS

| | | |
|---|---|---|
| DE | 3839859 | 8/1989 |
| EP | 2398411 | 12/2011 |

(Continued)

OTHER PUBLICATIONS

International Search Report dated Apr. 26, 2022 from International Application No. PCT/EP2021/085559.

(Continued)

*Primary Examiner* — Eduardo C Robert
*Assistant Examiner* — Steven J Cotroneo
(74) *Attorney, Agent, or Firm* — Beyer Law Group LLP

(57) ABSTRACT

The invention relates to a maxilla repositioning implant (1) for three-dimensional precise alignment of a maxilla displacing portion (5) relative to a remaining maxilla portion (3) that is fixed to the skull, wherein the maxilla repositioning implant (1) comprises a base (2), which has at least one plate (7) in which screw holes (10) are provided, wherein a portion of the material of the plate (7) defines, as a rim (11), a respective screw hole (10) that is provided for receiving a bone screw (17) in order to ensure fastening, via the bone screw (17) to be inserted into the respective screw hole (10), to the remaining maxilla portion (3) that is fixed to the skull, wherein the maxilla repositioning implant (1) also comprises a connection portion (4), which is spaced apart from the base (2) by connecting bridges (6), wherein the connection portion (4) comprises at least one plate (7) in which screw holes (10) are provided, and wherein a portion of the material of this plate (7) defines, as a rim (11), a respective screw hole (Continued)

Figure 1:
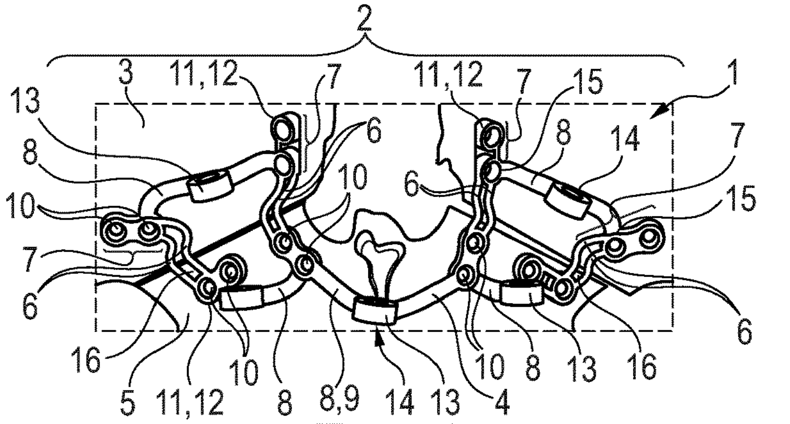

(10) in order to ensure fastening, via a bone screw (17) to be inserted into the respective screw hole (10), to the maxilla displacing portion (5), wherein two plates (7) and their connecting bridges (6) linking them are spanned in a rhombic manner.

15 Claims, 2 Drawing Sheets

(56) References Cited

U.S. PATENT DOCUMENTS

| | | | | |
|---|---|---|---|---|
| 8,257,355 | B2 * | 9/2012 | Chin | A61B 17/7059 606/284 |
| 8,784,456 | B2 | 7/2014 | Longepied | |
| 9,339,279 | B2 * | 5/2016 | Dubois | A61F 2/2875 |
| 10,869,705 | B2 | 12/2020 | Dubois et al. | |
| 2007/0238069 | A1 * | 10/2007 | Lovald | A61B 17/8085 606/281 |
| 2008/0281327 | A1 * | 11/2008 | Helfteren | A61B 17/8071 606/280 |
| 2011/0106169 | A1 * | 5/2011 | Zalenski | A61B 17/7074 606/279 |
| 2011/0144698 | A1 | 6/2011 | Buchbinder et al. | |
| 2011/0269100 | A1 * | 11/2011 | Furrer | A61B 17/8061 433/173 |
| 2011/0301609 | A1 * | 12/2011 | Longepied | A61B 17/8085 606/281 |
| 2012/0277748 | A1 * | 11/2012 | Trescony | A61B 17/80 606/70 |
| 2012/0277749 | A1 | 11/2012 | Mootien et al. | |
| 2013/0018425 | A1 * | 1/2013 | Seldin | A61B 17/8019 606/286 |
| 2015/0230843 | A1 * | 8/2015 | Palmer | A61B 17/7291 606/331 |
| 2016/0331427 | A1 * | 11/2016 | Waizenegger | A61B 17/8071 |
| 2017/0143393 | A1 * | 5/2017 | Hipp | A61B 17/8004 |
| 2017/0156770 | A1 * | 6/2017 | Stupak | A61B 17/8085 |
| 2017/0252176 | A1 * | 9/2017 | Tacca | A61B 17/7049 |
| 2018/0103965 | A1 | 4/2018 | Waizenegger | |
| 2018/0344464 | A1 | 12/2018 | Engstrad et al. | |
| 2019/0038414 | A1 * | 2/2019 | Johnston, Jr. | A61F 2/30942 |
| 2020/0345399 | A1 * | 11/2020 | Gregory, II | A61B 50/30 |

FOREIGN PATENT DOCUMENTS

| | | |
|---|---|---|
| EP | 2563242 | 3/2013 |
| EP | 2563244 | 3/2013 |
| EP | 2687168 | 1/2014 |
| EP | 2698122 | 2/2014 |
| EP | 2931143 | 6/2014 |
| EP | 2906129 | 8/2015 |
| EP | 2952145 | 12/2015 |
| EP | 3263050 | 1/2018 |
| EP | 3566663 | 11/2019 |
| FR | 2942125 | 8/2010 |
| FR | 2999071 | 6/2014 |
| JP | 2018515230 | 6/2018 |
| WO | WO 2014/043370 | 3/2014 |
| WO | WO 2014/090964 | 6/2014 |

OTHER PUBLICATIONS

German Search Report dated Jul. 28, 2021 from German Application No. DE 10 2020 134 240.3.
Written Opinion dated Apr. 26, 2022 from International Application No. PCT/EP2021/085559.

* cited by examiner

RHOMBUS-FORMING MAXILLA REPOSITIONING IMPLANT

The invention relates to a maxilla repositioning implant for three-dimensional, precise orienting of a maxilla displacing portion relative to a remaining maxilla portion fixed to the skull. As is customary, the maxilla here refers to the human upper jaw bone. A part of the upper jaw bone can be completely separated from the rest of the upper jaw via a surgical procedure. This allows a maxilla displacing portion to be removed from a remaining maxilla portion fixed to the skull. In this way, malpositions of the jaw can be corrected. However, the remaining maxilla portion has to be reattached to the maxilla displacing portion after displacing. For this purpose, maxilla repositioning implants are usually used.

Such maxilla repositioning implants are already known from various documents, such as EP 2 563 244 B1.

Disclosed therein is a preoperatively custom-made implant for use in orthognathic surgery. In orthognathic surgery, a first part of an upper jaw is separated from a second part of the upper jaw and the implant is then placed as part of this procedure. The implant comprises a plate component preformed to correspond to a preoperative shape of the upper jaw and includes a plurality of nonlinear undulations corresponding to predetermined surface parts of the first part of the upper jaw, wherein the plate component defines at least one fixation opening extending through the plate component and is adapted to receive a bone fixation element in order to fix the plate component to the first part of the upper jaw. Furthermore, a plurality of (free) fingers are provided extending away from the plate component, wherein the (free) fingers are preformed to correspond to the shape of the second part of the upper jaw and include a plurality of non-linear undulations corresponding to certain surface portions of the second part of the upper jaw.

Related documents disclose similar implants, such as EP 2 687 168 B1, EP 2 698 122 B1, EP 2 563 242 B1, EP 3 566 663 A2, EP 3 263 050 B1, EP 2 952 145 B1, EP 2 767 246 A1, EP 2 398 411 B1, FR 2 942 125 B1, WO 2014 090 964 A2, EP 2 931 143 A2, FR 2 999 071 A1, EP 2 906 129 B1, and WO 2014 043 370 A1.

However, the known implants always have disadvantages. In particular, these implants are difficult to manufacture. In addition, the stability is often insufficient. If the implants are installed on the bone and covered again with soft tissue material, such as skin and connective tissue, the result is an unaesthetic appearance, which in addition results in unpleasant wearing comfort for the patient. There are often complications and medically negative side effects.

Based on a maxilla repositioning implant with the following features, the object of the invention is to eliminate these disadvantages. In addition, a more cost-efficient maxilla repositioning implant is to be created while also eliminating other disadvantages.

The invention is based on a maxilla repositioning implant which has a base which has at least one plate in which screw holes are provided, wherein a portion of the material of the plate as a rim defines (i.e. partially or completely surrounds) a respective screw hole, wherein the screw hole is provided for receiving a bone screw in order to ensure fastening to the remaining maxilla portion fixed to the skull via the bone screw to be inserted into the respective screw hole, wherein the maxilla repositioning implant furthermore has a connection portion which is spaced from the base via connecting bridges, wherein the connection portion has at least one plate in which screw holes are also present and wherein a portion of the material of the plate as a rim defines a respective screw hole (i.e. partially or also completely surrounds the screw hole) in order to ensure fastening to the maxilla displacing portion via a bone screw to be inserted into the respective screw hole.

The object stated at the beginning is solved according to the invention in that two plates and their connecting bridges linking them are spanned in a rhombic manner, i.e. define a rhombic space/blank volume, so that a maxilla repositioning implant design with particularly high load-bearing capacity can be realized. In other words, the object is solved according to the invention in that connecting bridges extending from a plate, in particular from the at least one plate of the base, are formed obliquely to each other.

Such a maxilla repositioning implant enables higher strength with a tension-optimized design. It is also possible to use less material than with conventional implants. The surprising result is a more tissue-compatible design and the elimination of the disadvantages mentioned at the beginning. A solution completely different from EP 2 563 244 B1 with unexpectedly positive effects is achieved.

It should be remembered that both the base and the connection portion are adapted to the patient-specific geometry of the bone with regard to their side facing the maxilla. The surface contour of the maxilla, both in the area of the maxilla displacing portion and in the area of the remaining maxilla portion fixed to the skull, is determined via MRI, CRT and/or X-ray and copied into an identical contour of the plate of the base for the remaining maxilla portion fixed to the skull and the plate of the connection portion for the maxilla displacing portion using subsequent CAD/CAM manufacturing processes. Sintering processes such as laser sintering, for example the selective laser sintering process, can usually be used.

For protection abroad, in particular in the United States of America, it should be noted that the invention also covers a method for inserting the maxilla repositioning implant into/onto the patient.

However, the invention also relates to a method for manufacturing the maxilla repositioning implant.

Advantageous embodiments are claimed in the dependent claims and are explained in more detail below. It is also conceivable that these aspects are pursued further independently of the fact that two plates and their connecting bridges linking them are spanned in a rhombic manner, i.e. define a rhombic blank volume, but instead or in addition, (at least or only/exactly) two connecting bridges extend from the plate of the connection portion towards the rim of a (single/specific) screw hole in the plate of the base. However, it is of course preferred if this (these) combination(s) of features is (are) also realized in the embodiments of the dependent claims.

According to an advantageous embodiment, the connecting bridges extending from one plate may form an angle, preferably an acute angle, with each other.

It is also conceivable that the connecting bridges extending from the one plate run essentially parallel to each other in the area of the other plate.

In order to realize a design that is particularly kind to the tissue—in particular between screw hole attachment points on the bone—it has proven useful if each/the connecting bridge (preferably at at least one point or over the entire length of the connecting bridge) has an elliptical cross-section.

For manufacturing purposes, it is advantageous if the elliptical cross-section assumes the special shape of a circle at at least one point or over the entire length of the connecting bridge. It is also possible for flattenings to appear on the upper side of the connecting bridge facing away from the maxilla and/or for the elliptical cross-section to vary along its length. Elevations or depressions, in particular curvatures, may also be introduced. The advantageous result after insertion of the implant is a particularly aesthetic appearance when covering the implant or the implant sections with soft tissue.

It is beneficial for stability if the plate of the base and/or the plate of the connection portion has at least one point that has a greater thickness than the connecting bridge (in particular at its thickest point). In this context, it is also desirable that the connecting bridges are formed distinct from the components of the plate and/or that the area of the cross-section of the connecting bridge is between 70% or 80% and 120% (preferably 75% or 100%) of the area of the screw hole or the width of the connecting bridge is approximately equal to the diameter of one of the screw holes.

The precision of orienting the maxilla displacing portion relative to the remaining maxilla portion fixed to the skull is enhanced if each plate of the base and each plate of the connection portion are connected to each other by exactly two connecting bridges. Unintended stress such as bending and twisting, in particular in the event of almost unavoidable torsion of the base relative to the connection portion during insertion of the implant, will then not lead to malpositioning of the two maxilla portions. A particularly good medical result can thus be ensured.

If the connecting bridges run completely or mainly parallel to each other, a particularly tension-optimized design can be realized. The forces are then dissipated in the same way.

However, an advantageous embodiment is further characterized in that each connecting bridge has a first end and a second end, wherein the first end transitions as a single piece of material (integrally/uniformly) into the rim of a first screw hole of the base-side plate and the second end transitions as a single piece of material (integrally/uniformly) into the rim of a first screw hole of the plate on the connection portion side. Such a stepless geometry, which avoids inflammation for the patient, can then be realized. In addition, a high load-bearing capacity of the implant is ensured.

The invention further focuses on an embodiment characterized in that the base-side plate is connected to the connection-side plate via a first connecting bridge and a second connecting bridge, wherein the first connecting bridge and the second connecting bridge engage with their first ends at the rim of a single first screw hole of the base-side plate and a) either engage with their second ends together at the rim of a single first screw hole of the plate on the connection portion side/are attached thereto/are integrated therein or b) the one connecting bridge engages with its second end at the rim of the first screw hole of the plate on the connection portion side/is integrated therein and the other connecting bridge engages at the rim of a second screw hole of the plate on the connection portion side/is integrated therein. This embodiment thus offers two possibilities for realization, i.e. a particularly filigree variant (b) or a particularly stable variant (a). It also allows geometric peculiarities on the surface of the maxilla of the specific patient concerned to be taken into account. This results in particularly good patient-specific solutions.

It has proven useful if the second connecting bridge progressively increases in distance away from the first connecting bridge over its length as seen from the base-side plate (from at least near the first end in the direction near the second end) and, in a further development, comes closer to the first connecting bridge again in an area near the second end). Material thickening due to the proximity of the two connecting bridges can thus be prevented. In addition, it allows the stability to be increased.

Low material input while meeting the stability requirements can be realized if each plate has exactly 2 or more, but not more than 3, 4, 5 or 6 screw holes.

It is also advantageous if all plates have the same number of screw holes. This makes inserting the implant easier for the surgeon.

It is beneficial for the tolerability of the implant if the rim is formed as a bead. It is advantageous to form this bead further if it is (rather) concave on its side facing the screw hole. The head of the screw can then be flush with the surface of the implant facing away from the maxilla and rest on the implant without wobbling, i.e. precisely. The tolerability of the implant is thus significantly increased when bone screws are inserted.

This effect can be further enhanced if the bead is convex or cylindrical on its side facing away from the screw hole.

It is advantageous for manufacturing if each connecting bridge has at least one straight/linear/unbent portion in the longitudinal direction.

Such an implant can be particularly well adapted to the specific patient if two portions which are straight/linear/unbent in the longitudinal direction are connected via a (curved) arced portion, wherein the arced portion is advantageously prepared to bridge a 'Le-Fort-1 region' at a distance from the latter. Ultimately, this realizes an 'offset' which avoids incompatibilities in this Le-Fort-1 region.

It has proven useful if the straight portion or a curved portion of the connecting bridge forms the first end or the second end of the connecting bridge.

During testing of the elliptical cross-section, it has also proven successful if the main axis of the ellipse is between 25% and 75%, preferably 50% (+/−10%), larger than the secondary axis. This results in solutions that are particularly stable and allow good wearing comfort.

If the maxilla repositioning implant is dimensioned such that it is in contact with the maxilla only in the area of the rims of the screw holes, precise orienting of the two maxilla portions involved here (maxilla displacing portion and remaining maxilla portion fixed to the skull) can be achieved while avoiding unwanted pressure points and inflammation.

It is also advantageous if the connecting bridges are (materially) separated from each other (i.e. the connecting bridges are basically separate from each other) and are only attached to the connection portion via a first attachment area at their first end to the base via a second attachment area at their second end. The use of unnecessary amounts of material can then be avoided.

It is practical if the connecting bridges ensure a planar offset of an imaginary first plane receiving the screw hole at the base to an imaginary second plane receiving the screw hole in the connection portion.

It is advantageous if the longitudinal axis of a base-side plate predetermines the longitudinal axis of one or two connecting bridges extending therefrom, to which the longitudinal axis of the plate on the connection portion side, on which said connecting bridge engages or said connecting bridges engage, is aligned or extends transversely thereto—preferably orthogonally.

For manufacturing, but also for the tolerability of the implant, it is positive if the rims/beads of the screw holes (all) remain the same/uniform and/or are of the same thickness.

If two plates of the base are connected via a retaining bracket, the manipulability of the maxilla repositioning implant can be improved. In particular, the insertion process can be simplified. For example, the maxilla repositioning implant may then be placed as a uniform component—comprising at least one, better two, even better three or optimally 4, 5 or 6 plates at the base and at least one plate, better two plates, or even 3 or 4 or even 5 or 6 plates at the connection portion—via a retaining bracket, two retaining brackets in the area of the base, one retaining bracket in the area of the connection portion or even two or three retaining portions can be grasped by the surgeon and can be fixed as an integral component to the bone, specifically in the first step to the remaining maxilla portion fixed to the skull and then to the maxilla displacing portion or vice versa. During this procedure, the separation is to be carried out via cutting/milling measures on the maxilla between the maxilla displacing portion and the remaining maxilla portion fixed to the skull (preferably in the 'Le-Fort-1 area').

In the context of this operation, it has proven particularly advantageous when a retaining bracket is present on the connection portion side of the maxilla repositioning implant, which projects from one half of the face to the other, thus connecting the left and right parts.

It is particularly advantageous if two plates of the connection portion are connected to each other via a retaining bracket.

It is also advantageous if the retaining bracket is connected to the respective plate via a predetermined breaking point at the end side, since it can then be effortlessly broken out of the implant with simple measures and without cutting.

During the insertion process, it has proven to be advantageous if the retaining bracket itself (also) has a rounded contour.

Particularly advantageous embodiments can be realized if the retaining bracket a) has a plane surface facing the maxilla and a convex surface facing away from the maxilla or b) has an elliptical, preferably circular portion/cross-section.

For breaking out the retaining bracket from the inserted implant, i.e. for detaching the retaining bracket from the respective plates, it is advantageous if (at least/exactly) one eyelet is incorporated preferably in the center of the retaining bracket and when the longitudinal axis of it is oriented transversely—preferably orthogonally—to the longitudinal axis of the retaining bracket. In certain cases, it may be advantageous if the longitudinal axis of the eyelet is aligned with the longitudinal axis of the retaining bracket.

In the retaining bracket configuration, it is particularly advantageous if the retaining bracket remains at a distance from the maxilla while it is in a state fixed to the bone. In this way, sufficient clearance is maintained to ensure breaking out is possible in the inserted state and to avoid traumatization of the patient in the area of the retaining bracket.

If all plates of the connection portion are connected to each other via several retaining brackets, a compact maxilla repositioning implant can be realized, which can be handled precisely during surgery. Manipulability during the operation is facilitated.

It is advantageous if, on a single rim of a screw hole, two connecting bridges and a) one retaining bracket or b) two retaining brackets engage. It may also be preferable if c) a rim for a further/free screw hole is formed on a plate having this screw hole, from which neither connecting bridges nor retaining brackets extend (i.e. there are rims of screw holes which are free of connecting bridges and retaining brackets), or d) either two connecting bridges or at least one retaining bracket (preferably two retaining brackets) extend/extends from each rim of a screw hole.

It is advantageous if all plates are connected to each other via connecting bridges and/or retaining brackets. This results in a uniform maxilla repositioning implant with good manageability.

Stability is improved if each plate has only rims for the screw holes and, in addition, rims-connecting filling regions which are added to form a plate with straight ends. It is then practical to design the filling regions without protrusions. This prevents trauma and inflammation.

In addition, it is advantageous if two connecting bridges enclose a blank volume.

An advantageous embodiment is also characterized by the presence of a cavity between the rims of two screw holes of a plate and the adjacent filling regions. A particularly light maxilla repositioning implant using little material can then be designed, although sufficient stability is still present.

It is also advantageous if (at least or only/exactly) two (distinct/separated/connected on two sides) connecting bridges extend from the plate of the connecting portion towards the rim of a (single/specific) screw hole in the plate of the base.

Proven materials can be used if the implant is constructed of metal, such as a titanium or magnesium alloy, or is constructed of plastic, such as PPA, PLLA or PP. Magnesium alloys in particular, however, have unexpected advantages.

It is of course desirable to form the maxilla repositioning implant as a patient-specific implant, preferably using sintering techniques.

The concerned maxilla repositioning implant can be easily grasped on the retaining brackets. The plates and connecting bridges are adapted to the patient-specific geometry of the maxilla. A covering with soft tissue at the end of the operation has also been taken into account in advance. After opening the soft tissue in the region of the maxilla during surgery, the implant is attached to the maxilla and fixed via bone screws either to the maxilla displacing portion or to the remaining maxilla portion fixed to the skull. Before, during or after this, the separation of these two maxilla portions takes place. After displacing of the maxilla displacing portion relative to the remaining maxilla portion, which is unchanged in position and fixed to the skull, the implant is fixed to the maxilla portion that is still free at this point, i.e. either the remaining maxilla portion fixed to the skull or the maxilla displacing portion, via bone screws that are guided through the screw holes that are still free. A precise final position of the two maxilla portions relative to each other and fulfilling the medical wishes can then be realized. Before the implant is covered by soft tissue again, the retaining brackets are removed, e.g. via breaking out using the weakening in the area of the predetermined breaking points.

Figure 2:
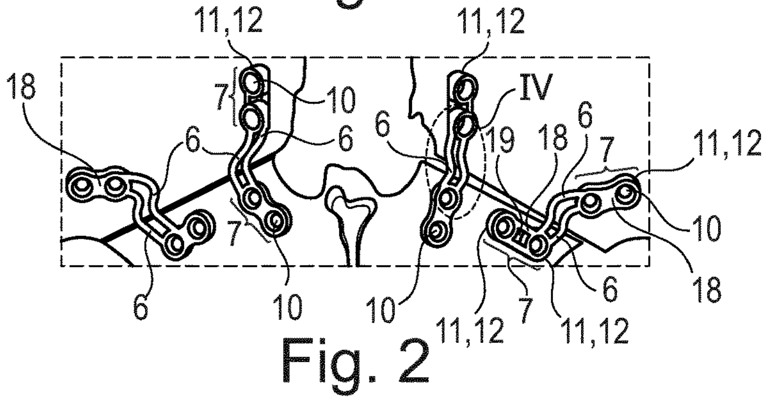
Figure 3:
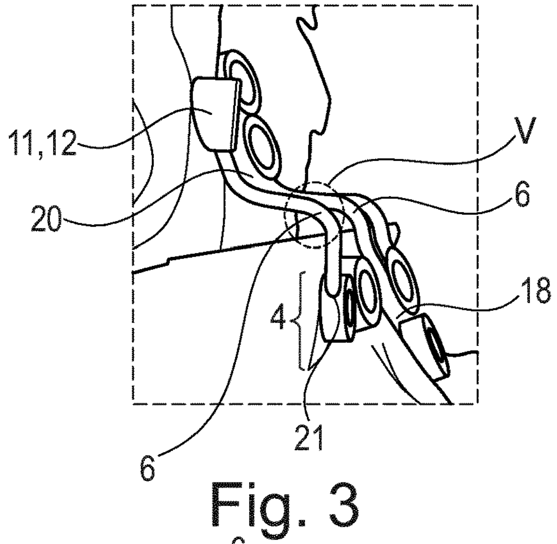
Figure 4:
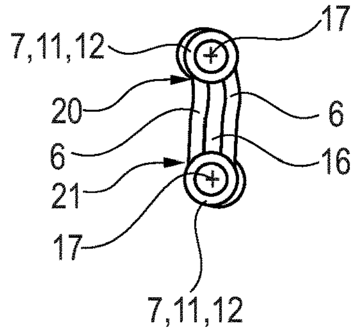
Figure 5:
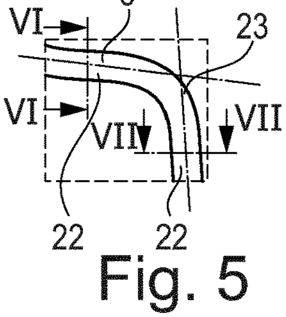
Figure 6:
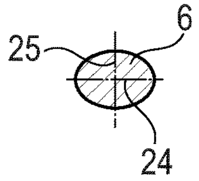
Figure 7:
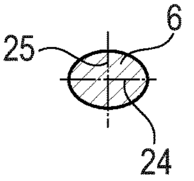
Figure 8:
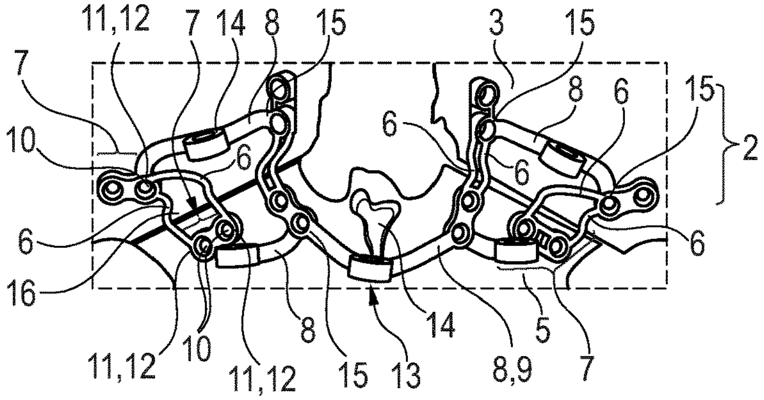
Figure 9:
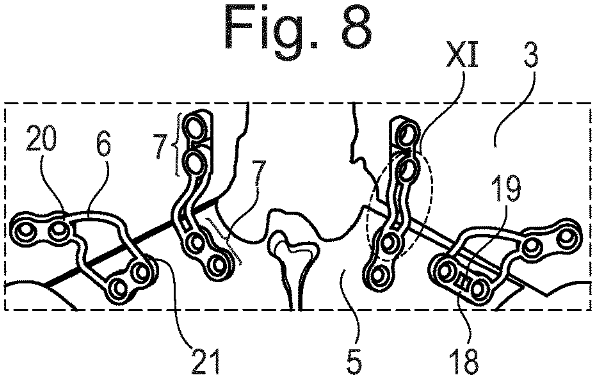
Figure 10:
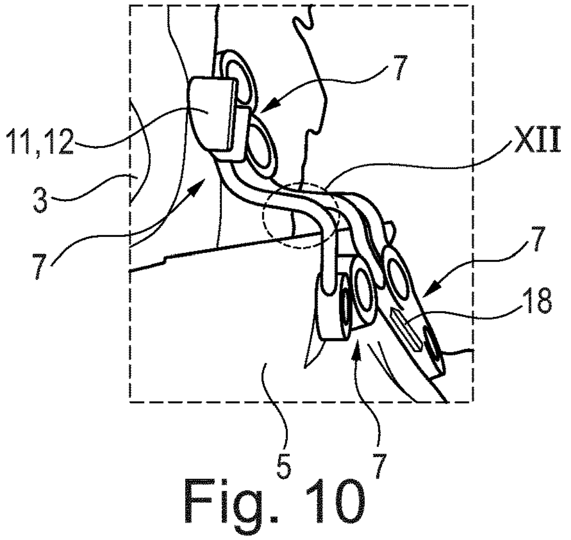
Figure 11:
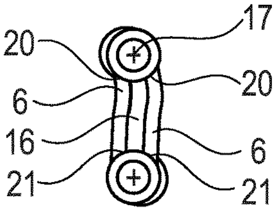
Figure 12:
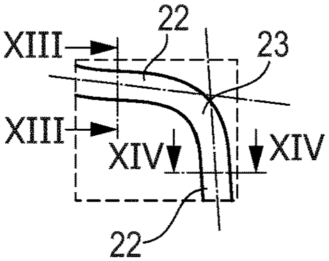
Figure 13:
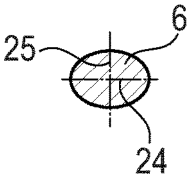
Figure 14:
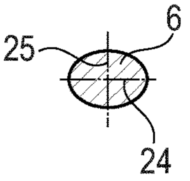

The invention is also explained in more detail below with the aid of a drawing. The following is shown:

FIG. 1 shows a first embodiment of a maxilla repositioning implant ('double-ridge concept') during insertion, FIG. 2 shows the maxilla repositioning implant with its plates of the base and the connection portion connected via connecting bridges, with the retaining brackets already removed, in a view comparable to FIG. 1, FIG. 3 shows a rotated representation of the inserted maxilla repositioning implant in the state shown in FIG. 2, FIG. 4 shows an enlargement of region IV of FIG. 2 with inserted bone screws, FIG. 5 shows a singular representation of the side of a single connecting bridge from FIG. 3, FIGS. 6 and 7 show cross-sections along lines VI and VII through the connecting bridge of FIG. 5, FIG. 8 shows a second embodiment of a maxilla repositioning implant according to the invention ('double-ridge concept with optimized path'), wherein the two connecting bridges connecting one plate of the base and one plate of the connection portion are spaced apart from each other, i.e. spread, ergo defining a rhombic blank volume, FIG. 9 shows a representation of the maxilla repositioning implant from FIG. 8 with the retaining brackets removed, FIG. 10 shows a side view of one half of the maxilla repositioning implant with removed retaining brackets to the state as shown in FIG. 9, FIG. 11 shows an enlargement of the area shown in FIG. 9 with inserted bone screws, FIG. 12 shows a lateral representation of one of the connecting bridges of FIG. 10, and FIGS. 13 and 14 show cross-sections along lines XIII and XIV through the respective connecting bridge of FIG. 12.

The FIGURES are of schematic nature only and are intended only for the understanding of the invention. Identical elements are provided with the same reference sign.

The first embodiment, described as a 'double-ridge concept', concerns a maxilla repositioning implant 1. The maxilla repositioning implant with a base 2 engages a remaining maxilla portion 3 fixed to the skull. A connection portion 4 of the maxilla repositioning implant 1 engages a maxilla displacing portion 5. The remaining maxilla portion 3 fixed to the skull and the maxilla displacing portion 5 are parts of the maxilla, i.e. the upper jaw.

The connection portion 4 is spaced from the base 2 of the maxilla repositioning implant 1 by connecting bridges 6. The connecting bridges 6, of which there are eight in the present configuration example, engage plates 7.

Four plates 7 belong to the base 2 and four plates 7 belong to the connection portion 4. Two, three, four, five, six, seven or even eight plates 7 may be used per base 2 or per connection portion 4. In the present configuration example, there are the same number of plates 7 in the base 2 and connection portion 4, i.e. four in each case. However, the numbers may be different. In the illustrated embodiment, the plates are solid unitary structures.

There are also retaining brackets 8 that connect the plates 7 of the base 2 with each other or connect the plates 7 of the connection portion 4 with each other. Ultimately, the retaining brackets 8 are used in such a way that at least two plates 7 of the base 2 or of the connection portion 4 are always connected to each other. Furthermore, there is a central retaining bracket 8, which is additionally designated with the reference sign 9 and which ensures the connection of the left half of the maxilla repositioning implant 1 with the right half of the maxilla repositioning implant 1 in the area of the connection portion 4. The arrangement of the central retaining bracket 9 as part of the connection portion 4 is advantageous, since the component can then be arranged below the nose, which realizes a relatively good wearing comfort and appearance.

Returning to the connecting bridges 6, it is significant that there are preferably two screw holes 10 in each of the plates 7. The screw holes 10 are formed by the material of the plates 7. The material of the plates 7 defines a rim 11 for the respective screw hole 10. The rim 11 is formed as a bead 12. It should be noted that each plate 7 should have more than two screw holes 10.

Eyelets 13 are provided in the transition region between the retaining brackets 8, i.e. also the central retaining bracket 9, and the respective plates 7. The eyelets 13 have longitudinal axes that are provided with the reference sign 14. There are predetermined breaking points 15 in the transition region between the retaining brackets 8 and the plates 7. These are shown as an example on one retaining bracket 8, but exist on most or better all retaining brackets 8.

The connecting bridges 6 always extend from a plate 7 of the base 2, and ensure a connection with the rim 11 of a plate 7 of the connection portion 4.

In the configuration example of FIG. 1, the connecting bridges 6 of one plate 7 run (predominantly) parallel to the other plate 7, wherein their first end in the rim 11 of one plate 7 terminates in the rim 11 of a single screw hole and their second end terminates in the rim 11 of the bead 12 of a single screw hole 10 of the (other) plate 7 of the connection portion 4. In other words, both connecting bridges 6 always connect a single rim of a single screw hole 10 of one plate 7 with the rim 11 of a single screw hole 10 of the other plate 7. The connecting bridges 6 always occur in pairs. There are blank volumes 16 between the connecting bridges 6.

These blank volumes are also clearly visible in FIG. 4, where the inserted bone screws 17 are also indicated.

FIG. 2 shows the state without retaining brackets after completion of the operation.

The individual rims 11 around the screw holes 10 are completed by filling regions 18 connecting them to form the respective plate 7. It is noticeable that on at least one of the plates 7 of the connection portion 4, those filling regions 18 closing the rims 11 to form the plate leave a cavity 19 free.

FIG. 3 clearly shows that the rims 11 are cylindrical on the outside, at least in terms of their external contour, but have a concave shape on the inside that is adapted to a screw head.

In FIG. 5, it is indicated that at least one of the connecting bridges 6, preferably all connecting bridges 6, have a straight portion 22 and at least one arced portion 23 between a first end 20 of the connecting bridge 6 and a second end 21 of the connecting bridge 6 (see in this respect FIG. 3).

The fact that the cross-section of the connecting bridge 6, preferably of all connecting bridges 6, remains the same over its length and does not vary from connecting bridge 6 to connecting bridge 6 can be seen from FIGS. 5 to 7. The main axis 24 is larger than the secondary axis 25 by a factor of 11:8.

The embodiment as shown in FIGS. 8 to 14 and designated as 'double-ridge concept with optimized path' is particularly characterized by the enlargement of the blank volumes 16 such that the connecting bridges 6, each connecting two plates 7, tend to increase in distance away from each other in the direction of the connection portion 4. In this case, the one connecting bridge 6 extends from the rim 11 of a base-side plate 7 around a single screw hole 10 there to a rim 11 around a first screw hole 10 in the plate 7 of the connection portion 4, whereas the other connecting bridge 6, which extends from the same rim 11 around the screw hole 10 from which the first connecting bridge 6 extends, to another rim 11 of another screw hole 10 of the same plate 7 of the connection portion 4, seen relative to the first connecting bridge 6. The blank volume 16 then has a more rhombic shape. The one connecting bridge 6 and the other connecting bridge 6 then start from the same rim 11 of the screw hole 10 of the base 2, but end at different rims 11 of different screw holes 10 of the same plate 7 of the connection portion 4.

LIST OF REFERENCE SIGNS

1 maxilla repositioning implant
2 base

3 remaining maxilla portion fixed to the skull
4 connection portion
5 maxilla displacing portion
6 connecting bridge
7 plate
8 retaining bracket
9 central retaining bracket
10 screw hole
11 rim
12 bead
13 eyelet
14 longitudinal axis
15 predetermined breaking point
16 blank volume
17 bone screw
18 filling region
19 cavity
20 first end of the connecting bridge
21 second end of the connecting bridge
22 straight portion of the connecting bridge
23 arced portion of the connecting bridge
24 main axis
25 secondary axis

The invention claimed is:

1. A maxilla repositioning implant for three-dimensional precise orienting of a maxilla displacing portion relative to a remaining maxilla portion fixed to the skull, wherein the maxilla repositioning implant is suitable for use in reattaching the maxilla displacing portion that was surgically separated from the remaining maxilla portion to correct a malposition of a jaw, and wherein the maxilla repositioning implant is a single unitary structure and comprises:

a base which has at least a first base plate in which at least two base plate screw holes are provided, wherein each base plate screw hole has an associated base plate screw hole rim formed from a portion of the material of the first base plate for receiving an associated bone screw to enable fastening the base to the remaining maxilla portion fixed to the skull via the associated bone screw, and wherein the first base plate is a solid unitary structure; and a connection portion which is spaced from the base via first and second connecting bridges, wherein the connection portion has at least a first connection portion plate in which at least two connection plate screw holes are provided and wherein each connection plate screw hole has an associated connection plate screw hole rim formed from a portion of the material of the first connection portion plate to enable fastening to the maxilla displacing portion via the associated bone screw, and wherein the first connection portion plate is a solid unitary structure; and wherein the first and second connecting bridges extend obliquely relative to one another from a first one selected from the group consisting of the first base plate and the first connection portion plate and form an angle relative to one another where they extend from a second one selected from the group consisting of the first base plate and the first connection portion plate, to define a three- dimensional blank volume therebetween when the maxilla repositioning implant is surgically attached to both the remaining maxilla portion and the maxilla displacing portion.

2. The maxilla repositioning implant according to claim 1, wherein the connecting bridges have an elliptical cross-section.

3. The maxilla repositioning implant according to claim 2, wherein the elliptical cross-section assumes the specific shape of a circle.

4. The maxilla repositioning implant according to claim 1, wherein the first base plate and the first connection portion plate each have at least one point which has a greater thickness than the connecting bridges.

5. The maxilla repositioning implant according to claim 1, wherein each plate of the base and each plate of the connection portion are connected to each other via exactly two connecting bridges.

6. The maxilla repositioning implant according to claim 1, wherein the connecting bridges run parallel to each other over a majority of their respective lengths.

7. The maxilla repositioning implant according to claim 1, wherein each connecting bridge has a first end and a second end, wherein the first end transitions as a single piece of material into the rim of a first screw hole of the first base plate and the second end transitions as a single piece of material into the rim of a first screw hole of the first connection portion plate on the connection portion side.

8. The maxilla repositioning implant according to claim 1, wherein first ends of the first connecting bridge and the second connecting bridge engage with the rim of a single first screw hole of the first base plate and a) either second ends of the first connecting bridge and the second connecting bridge engage together at the rim of a single first screw hole of the first connection portion plate, or b) the second end of the first connecting bridge engages the rim of the first screw hole of the first connection plate and the second end of the second connecting bridge engages the rim of a second screw hole of the first connecting portion plate.

9. The maxilla repositioning implant according to claim 8, wherein the second connecting bridge progressively increases in distance away from the first connecting bridge over the length as seen from the first base plate.

10. The maxilla repositioning implant according to claim 1, wherein each plate has exactly two or more screw holes.

11. The maxilla repositioning implant according to claim 1 wherein the blank volume is rhombic.

12. The maxilla repositioning implant according to claim 1 wherein the maxilla repositioning implant is suitable for use in reattaching the maxilla displacing portion that was separated from the remaining maxilla portion by osteotomy.

13. The maxilla repositioning implant according to claim 1, wherein: first ends of the first connecting bridge and the second connecting bridge engage with the rim of a single first screw hole of the first base plate and the second end of the first connecting bridge engages the rim of the first screw hole of the first connection plate and the second end of the second connecting bridge engages the rim of a second screw hole of the first connecting portion plate.

14. A maxilla repositioning implant for three-dimensional precise orienting of a maxilla displacing portion relative to a remaining maxilla portion fixed to the skull, wherein the maxilla repositioning implant is suitable for use in reattaching the maxilla displacing portion that was surgically separated from the remaining maxilla portion to correct a malposition of a jaw, and wherein the maxilla repositioning implant is a single unitary structure and comprises:

a base which has at least a first base plate in which at least two base plate screw holes are provided, wherein each base plate screw hole has an associated base plate screw hole rim formed from a portion of the material of the first base plate for receiving an associated bone screw to enable fastening the base to the remaining maxilla portion fixed to the skull via the associated bone screw, and wherein the first base plate is a solid unitary structure; and a connection portion which is spaced from the base via first and second connecting bridges, wherein the connection portion has at least a first connection portion plate in which at least two connection plate screw holes are provided and wherein each connection plate screw hole has an associated connection plate screw hole rim formed from a portion of the material of the first connection portion plate to enable fastening to the maxilla displacing portion via the associated bone screw, and wherein the first connection portion plate is a solid unitary structure; and wherein the first and second connecting bridges extend obliquely relative to one another from a first one selected from the group consisting of the first base plate and the first connection portion plate and run substantially parallel to each other where they extend from a second one selected from the group consisting of the first base plate and the first connection portion plate, to define a three-dimensional blank volume therebetween when the maxilla repositioning implant is surgically attached to both the remaining maxilla portion and the maxilla displacing portion.

15. A maxilla repositioning implant for three-dimensional precise orienting of a maxilla displacing portion relative to a remaining maxilla portion fixed to the skull, wherein the maxilla repositioning implant is suitable for use in reattaching the maxilla displacing portion that was surgically separated from the remaining maxilla portion by osteotomy to correct a malposition of the jaw, and wherein the maxilla repositioning implant is a single unitary structure and comprises:

a base having a plurality of base plates, each base plate being a solid unitary structure that includes at least two base plate screw holes, wherein each base plate screw hole has an associated base plate screw hole rim formed from a portion of the material of the base plate for receiving an associated bone screw to facilitate fastening the base to the remaining maxilla portion fixed to the skull; and a connection portion having a plurality of connection portion plates, each connection portion plate being a solid unitary structure that includes at least two connection portion plate screw holes, wherein each connection portion plate screw hole has an associated connection portion plate screw hole rim formed from a portion of the material of the connection portion plate for receiving an associated bone screw to facilitate fastening the connection portion to the maxilla displacing portion; and a plurality of sets of connecting bridges, each connecting bridge set including a pair of connecting bridges that directly connect an associated one of the base plates to an associated one of the connection portion plates, and wherein the connecting bridges in at least one of the connecting bridge sets extend obliquely relative to one another as they emanate from the associated base plate to define a three-dimensional blank volume therebetween when the maxilla repositioning implant is surgically attached to both the remaining maxilla portion and the maxilla displacing portion.

* * * * *